United States Patent [19]
Cooper et al.

[11] Patent Number: 5,892,228
[45] Date of Patent: Apr. 6, 1999

[54] PROCESS AND APPARATUS FOR OCTANE NUMBERS AND REID VAPOR PRESSURE BY RAMAN SPECTROSCOPY

[75] Inventors: John B Cooper, Virginia Beach, Va.; Roy R Bledsoe, Jr., Huntington, W. Va.; Kent L Wise, Portsmouth, Va.; Michael B Sumner, Huntington, W. Va.; William T Welch; Brian K Wilt, both of Ashland, Ky.

[73] Assignees: Ashland Inc., Ashland, Ky.; Old Dominion University Research Foundation, Norfolk, Va.

[21] Appl. No.: 724,726

[22] Filed: Sep. 30, 1996

[51] Int. Cl.⁶ .................................................... G01N 21/35
[52] U.S. Cl. ............................... 250/339.12; 250/339.09; 250/339.11; 250/343; 356/301
[58] Field of Search .......................... 250/339.09, 339.11, 250/339.12, 343; 356/301

[56] References Cited

U.S. PATENT DOCUMENTS

| | | |
|---|---|---|
| 4,963,745 | 10/1990 | Maggard . |
| 5,121,337 | 6/1992 | Brown ................................. 250/339.12 |
| 5,139,334 | 8/1992 | Clarke ........................................ 356/301 |
| 5,349,188 | 9/1994 | Maggard ............................ 250/339.12 |
| 5,596,196 | 1/1997 | Cooper et al. ...................... 250/339.12 |

OTHER PUBLICATIONS

Angel et al., "Simultaneous Mulit–Point Fiber–Optic Raman Sampling for Chemical Process Control Using Diode Lasers and a CCD Detector", SPIE vol. 1857, Chemical, Biochemical, and Environmental Fiber Sensors 111, 1991, pp. 219–231.

"Determination of Method and Methyl tert–Butyl Ether in Gasoline by–Infrared Spectors . . . ", F.X. Garcia, LD Lima, JC Medine, Appl. Spectr. 1036 (1993).

"Determination of Octane Number and Reid Vapor Pressure . . . ", Cooper, Wise, Gorves and Welch, Analytical Chem. vol. 67, No. 22, Nov. 15, 1995.

"Determination on Weight Percent Oxygen in Commercial Gasoline . . . ", Cooper Wise, Welch, Bledsoe, Summery J. Appl. Spectroscopy. vol. 50, No. 7, Jul. 1996.

Primary Examiner—Constantine Hannaher
Attorney, Agent, or Firm—Richard C. Willson, Jr.; Richard D. Stone; A. J. Adamcik

[57] ABSTRACT

A Fourier-Transform Raman spectrometer was used to collect the Raman spectra of (208) commercial petroleum fuels. The individual motor and research octane numbers (MON and RON, respectively) were determined experimentally using the industry standard ASTM knock engine method. Partial Least Squares (PLS) regression analysis can be used to build regression models which correlate the Raman spectra (175) of the fuels with the experimentally determined values for MON, RON, and pump octane number (the average of MON and RON) of the fuels. Each of the models was validated using leave-one-out validation. The standard errors of validation (SEV) are 0.415, 0.535, and 0.410 octane numbers for MON, RON, and pump octane number, respectively. By comparing the standard error of validation to the standard deviation for the experimentally determined octane numbers, it is evident that the accuracy of the Raman determined values is limited by the accuracy of the training set used in creating the models. The Raman regression models were used to predict the octane numbers for the fuels which were not used to build the models. The results compare favorably with the leave-one-out validation. Also, it is demonstrated that the experimentally determined Reid Vapor Pressures are highly correlated with the Raman spectra of the fuel samples and can be predicted with a standard error of 0.568 psi.

46 Claims, 10 Drawing Sheets

PROCESS AND APPARATUS FOR OCTANE NUMBERS AND REID VAPOR PRESSURE BY RAMAN SPECTROSCOPY

CROSS REFERENCE TO RELATED APPLICATIONS

U.S. patent application Ser. No. 08/432,559, filed May 1, 1995, U.S. patent application Ser. No. 08/449,326, filed May 24, 1995; and U.S. Provisional patent application Ser. No. 60/002,649, filed Aug. 22, 1995, later as U.S. Ser. No. 08/657,489, relate to the general field of the present invention. These applications are incorporated herein by reference.

BACKGROUND OF THE INVENTION

I. Field of the Invention

The present invention relates to the field of analysis of physical and chemical properties of mixtures comprising hydrocarbons, preferably petroleum fuels, by use of Raman spectroscopy, preferably FT-Raman spectroscopy.

The instrument can utilize spectrometers of the Fourier-Transform (FT) Raman variety or of the Dispersive Raman variety or can use Hadamard Transform Raman spectrometers or other spectroscopic techniques known in the art.

Hadamard Transform spectroscopy is described in a paper by Hammaker et al. in Vibrational Spectra and Structure, Vol. 15, November 1986, " . . . The purpose of the spectrum analyzer is to disperse the near infrared radiation passing through the body into its spectral components. Selected wavelength ranges are focused on detector cells, which provide an analog signal proportional to the intensity of radiation in the selected wavelength . . . " (taken from U.S. Pat. No. 5,379,764 to Barnes et. al.)

II. Description of the Prior Art

The Clean Air Act of 1989 has mandated radical change in the petroleum refinery industry. Based on seasonal and geographical considerations, commercial gasoline blends must meet stringent environmental requirements while at the same time providing automotive compatibility and efficiency (Rhodes, A. K. Oil & Gas Journal, 17 Jan. 1994, 16). Conventional methods of determining these characteristics of a fuel are time consuming and expensive. Examples include determining total aromatics and olefins via gas chromatography; determining octane numbers via ASTM knock engine methods; and determining vapor pressure via the Grabner method. Legislators realize the need to improve efficiency and lower costs for these measurements and accordingly allow refineries to use alternative methods which are not approved by the EPA if the alternative methods are accepted by the industry.

As early as 1950, Raman spectroscopy was proposed as a method to determine aromatics and olefins in hydrocarbon mixtures (Heigl, J. J.; Black, J. F.; Dudenbostel, B. F.; U.S. Pat. No. 2,527,122, 24 Oct. 1950). However, until recently, extensive use of Raman spectroscopy in the characterization of hydrocarbons has not been practical. One early limitation to Raman analysis was the absence of a high intensity and stable excitation source. This problem has been overcome with the advent of lasers. Another limitation was the presence of fluorescence in hydrocarbon fuels when excited by visible lasers. The development of Fourier-Transform Raman spectrometers, however, now allows Raman spectra to be collected using NIR lasers (e.g. the Nd:YAG laser emitting at 1064 nm) which eliminate or severely reduce fluorescence in petroleum fuels.

Recently, Raman spectroscopy has been demonstrated as a viable quantitative technique in the analysis of analytes which are present in liquid mixtures as minor components (Shope, R.; Vickers, T. J.; Mann, C. K., 42, Appl. Spectrosc., 1988, 468). Chung, Clarke and others have demonstrated that Raman spectroscopy can be used in the qualitative analysis of aviation fuel for the determination of general hydrocarbon makeup, aromatic components, and additives (Chung, W. M.; Wang, Q.; Sezerman, U.; Clarke, R. H., 45, Appl. Spectrosc., 1991, 1527; Clarke, R. H.; Chung, W. M.; Wang, Q.; DeJesus, S.; Sezerman U., 22, J of Raman Spectrosc., 1991, 79). Williams and coworkers have shown that FT-Raman spectroscopy in combination with chemometrics can be used to determine gas-oil cetane number and cetane index (Williams, K. P. J.; Aries, R. E.; Cutler, D. J.; Lidiard, D. P., 62, Anal. Chem., 1990, 2553). In addition, Seasholtz et. al. have demonstrated quantitative analysis of the percentage of each fuel in fuel mixtures containing three unleaded gasolines (Seasholtz, M. B.; Archibald, D. D.; Lorber, A.; Kowalski, B. R., 43, Appl. Spectrosc., 1989, 1067). Despite these investigations, Raman spectroscopy is still not significantly utilized in the industrial analysis of petroleum fuels.

In contrast, NIR absorbance\reflectance spectroscopy has gained wide acceptance in the industrial analysis of octane number during the blending process (S. M. Maggard, U.S. Pat. No. 5,349,188, 9 Apr. 1990; S. M. Maggard, U.S. Pat. No. 4,963,745, 16 Oct. 1990). Multivariate analysis of NIR spectra currently provides real-time feedback for on-line process control of blending operations (as well as other processes) at a number of refineries, including the Ashland Petroleum refineries in Catlettsburg, Kentucky, and St. Paul, Minn. Despite the success of NIR spectroscopy in the petroleum industry, NIR also has certain limitations. For example, the overtone absorbances which constitute a NIR spectrum are typically broad and ill-resolved. This results in a decrease in the "chemical information" contained in the spectral data. Applicants have recently shown that fiber-optic Raman spectroscopy with partial least squares analysis is capable of quantifying individual octane numbers and RVP (with standard errors <0.5% vol) in hydrocarbon blends. This advantage over NIR spectroscopy is due to the abundant, yet sharp and well resolved, spectral peaks in the Raman spectra.

Applicants herein describe the use of FT-Raman spectroscopy and the preferred partial least squares (PLS) regression analysis to accurately determine the research octane number (RON), the motor octane number (MON), the pump octane number (PUMP), and the Reid Vapor Pressure (RVP) of 208 commercial petroleum fuel blends produced by the Ashland Petroleum Company.

Kelly et al. used a NIR instrument equipped with fiber-optics to gather spectra for predicting octane after multivariate treatment. See F. X. Garcia, L. D. Lima, and J. C. Medina, 47, Appl. Spectrosc., 1036 (1993). Williams et al. have shown that NIR FT-Raman spectroscopy combined with multivariate statistics can be used to determine the gas oil cetane number and cetane index. See J. B. Cooper, K. L. Wise, J. Groves, and W. T. Welch, Anal. Chem., 16 (22), Nov. 15, 1995. Garcia et al. used mid-IR absorption spectroscopy and partial least squares regression analysis to model percent oxygenates in fuel samples. See J. B. Cooper, K. L. Wise, W. T. Welch, R. R. Bledsoe and M. B. Sumner, Appl. Spectrosc. 50 (7), July 1996. Fiber-optic NIR reflecto-absorbance spectroscopy in tandem with multiple linear regression is used at Ashland Petroleum to monitor the concentration of aromatics and octane number in real time.

Applicants have also recently demonstrated that FT-Raman and PLS regression analysis can be used to predict oxygenate concentrations, octane numbers, and Reid vapor pressure in commercial gasolines with a degree of accuracy similar to NIR methods. See 1988 Annual Book of ASTM Standards, Vol. 05.04.

SUMMARY OF THE INVENTION

I. General Statement of the Invention

According to the invention, a Fourier-Transform Raman spectrometer is used to collect the Raman spectra of (208) commercial petroleum fuels. The individual motor and research octane numbers (MON and RON, respectively) are determined experimentally using the industry standard ASTM knock engine method. Partial Least Squares (PLS) regression analysis can be used to build regression models which correlate the Raman spectra (175) of the fuels with the experimentally determined values for MON, RON, and pump octane number (the average of MON and RON) of the fuels. Each of the models is validated using leave-one-out validation. The standard errors of validation are 0.415, 0.535, and 0.410 octane numbers for MON, RON, and pump octane number, respectively. By comparing the standard error of validation to the standard deviation for the experimentally determined octane numbers, it is evident that the accuracy of the Raman-determined values is limited by the accuracy of the training set used in creating the models. The Raman regression models are used to predict the octane numbers for the fuels which are not used to build the models. The results compare favorably with the leave-one-out validation. Also, it is demonstrated that the experimentally determined Reid Vapor Pressures are highly correlated with the Raman spectra of the fuel samples and can be predicted with a standard error of 0.568 psi.

The resulting correlation models predict the octane numbers remarkably well. This is evident both in the standard errors of validation for the models determined with leave-one-out validation as well as by the prediction of the test set. In both cases the standard error is comparable to the standard deviation for the experimentally determined values (0.4 octane numbers). This suggests that in this work, the ability of Raman spectroscopy to predict the octane numbers of commercially available fuels is limited primarily by the accuracy of the training set. It is reasonable to expect that if the accuracy of the octane values in the training set is improved, the standard errors for the models will be reduced even further.

Of the 208 petroleum fuels, only five exhibit any fluorescence when excited with 1064 nm radiation. This is attributable to the long wavelength of the laser. Applicants have also measured the Raman spectra of 100 of these fuels using a dispersive Raman instrument with excitation at 852 nm and have found that 10% of these samples exhibit significant fluorescence. Since longer wavelength excitation is not presently practical for a dispersive system, the use of a Fourier-Transform instrument is preferred when collecting Raman spectra of highly colored petroleum fuels. Even in the case of the five fluorescent samples (using the FT-Raman), the fluorescence is weak and decays to the baseline in the CH stretching region of the spectrum. As shown in Table 2, a model constructed using the entire spectral region (fingerprint and CH stretching regions) results in large prediction errors for these samples. If the region between the fingerprint and CH stretching regions is eliminated from the model, the error improves but is still relatively high. By using only the baseline corrected CH stretching region, however, the models become highly accurate in predicting the octane numbers. In the construction of all of the partial least squares regression models, the spectra are mean-centered and variance scaled prior to processing. For the present and previous work in Applicants' laboratories, this has resulted in more accurate and robust models than if other or no preprocessing of the data was performed. Applicants believe that the primary reason for this improvement is the existence of slight intensity changes due to variations in the laser power during the collection of the Raman spectra of the training set. Although it is possible to rigorously control the laser output in the laboratory environment and therefore yield more accurate models, the models will not be as robust unless the spectra of the samples to be predicted are subjected to the same rigorous control of the laser intensity. This is not likely to be the case for many industrial applications.

Accepting that some degree of laser intensity variation is inevitable in an industrial application, it is still possible to improve the performance of the system via calibration. As an extreme example, Applicants have acquired the Raman spectra of one of the fuel samples using laser powers of both 250 and 450 mW. These spectra represent extremes in laser power variations. In addition, the spectrum of toluene is acquired under the same conditions as the spectra in the training set (380 mW) as well as at 250 and 450 mW. The intensity of the strongest toluene peak in the CH stretching region (the calibration peak) is used to construct a calibration ratio for the extreme spectra by dividing the calibration peak intensity acquired under training set conditions by the calibration peak intensity acquired under one of the extreme laser power conditions. This ratio is then multiplied times all of the intensities in the extreme spectrum of the petroleum sample to give a normalized spectrum. In both cases (250 and 450 mW) the models predict the octane numbers as well as if the spectrum had been acquired under similar laser power conditions. Without the calibration step, the extreme spectra result in predicted octane numbers with high errors.

FT-Raman spectroscopy in combination with partial least squares regression analysis can be used to construct highly correlated models relating a petroleum fuel's Raman spectrum to its motor octane number, its research octane number, its pump octane number, and its Reid Vapor Pressure. Using leave-one-out validation, the standard errors for MON, RON, and PUMP are 0.415, 0.535, and 0.410 octane numbers, respectively. For the Reid Vapor Pressure model the standard error of validation is 0.568 psi. Using a blind test set of 20 petroleum fuels, the regression models predict MON, RON, and PUMP with average absolute errors of 0.389, 0.383, and 0.365 octane numbers, respectively. Using the same blind test set, the Reid Vapor Pressure model yields an average absolute error of 0.425 psi.

For the experimentally determined RON and MON values, the average standard deviation is 0.4 octane numbers. This suggests that the regression models are limited primarily by the accuracy of the training sets. This is comparable to the accuracy reported for NIR absorbance/reflectance methods currently being used by the petroleum refinery industry (S. M. Maggard, U.S. Pat. No. 5,349,188, 9 Apr. 1990; S. M. Maggard, U. S. 4,963,745, 16 Oct. 1990).

In the present study, no preclassification of fuels is performed. Of the 208 fuels utilized in the study, 79 of the samples are oxygenated with methyl-t-butylether (MTBE). Hence Raman spectroscopy has the demonstrated ability to quantitate octane numbers and vapor pressure across a diverse range of fuel compositions with a single multivariate model for each property being quantified.

Raman vs. NIRA

In comparing the accuracy of the two methods (NIRA and Raman), the two methods are comparable for the determination of octanes and RVP. Raman spectra are not compensated for small laser intensity variations during the collection of data. Such variations in the laser source introduce error. In the case of NIRA spectroscopy, the source variations are compensated for by ratioing the sample signal to a background or blank signal. Despite this slight advantage of NIRA over Raman, the accuracies are still comparable.

There are significant practical advantages of Raman over NIR for on-line process control.

1) Glass does not interfere with the Raman Technique. This allows the use of commercial communication grade fiber optics to transport the laser to the process and return the signal from the process. This means that the instrument can be set up in a normal environment (without any of the precautions necessary for an environment which contains petroleum products) and the fiber optics can be routed to processes which are several hundred feet away much more inexpensively compared to Near-IR and only two are required for each process to be monitored.

2) Raman is a scattering process and hence does not require reflective mirrors or a defined pathlength as required by Near-IR. This means that the laser exits the probe and scatters off of the sample back into the probe. This makes it easy to design a simple fitting for process lines. It also greatly reduces the effect of fouling of the optics.

3) If slugs of water enter the process stream, the Raman signal will drop to a low value. On-line Raman predictions based on such signals will give an obvious indication of this abnormal sample condition. On the other hand, near-IR octane predictions under these circumstances, while being meaningless, will resemble those for normal samples and may not be noticed by the operator.

In this application, Applicants describe results which demonstrate that fiber-optic NIR dispersive Raman spectroscopy coupled with multivariate regression analysis can be used to rapidly and remotely determine pump octane number, research octane number, motor octane number, and Reid vapor pressure in fuel samples. The NIR region is attractive for Raman spectroscopy because it minimizes fluorescence, and because it exhibits low attenuation in fiber-optics. The ability of NIR to be carried through fiber-optics is an important feature because it offers the possibility of installing adaptable fiber-optic probe systems on-line for process control during blending and reforming processes. In addition, the described dispersive Raman system is cost competitive with commercial NIR systems.

As illustrated in Example 3, a low cost dispersive Raman instrument with CCD detection, Distributed Bragg Reflector (DBR) diode laser excitation, and remote fiber-optic sampling can be used, preferably in conjunction with PLS regression models, to predict the octane numbers and RVP of commercial gasolines. RON, MON, Pump and Reid vapor pressure can be determined with standard errors of 0.77, 0.42, 0.52, and 0.60, respectively, preferably using a first derivative transform and mean-centering. This is comparable to the error associated with the ASTM knock engine method (0.4 octane numbers).

The total components cost of the described instrument is competitive with commercial NIR instrumentation. One of the main features of the described instrumentation is the inexpensive DBR diode laser which is immune to mode hops and hysteresis. The use of a CCD two-dimensional array detector also allows for the possibility of sampling at multiple stream locations simultaneously with a single instrument. When combined with fiber-optic sampling, the system provides a viable method for remote on-line industrial process control.

II. Utility of the Invention

Table A summarizes preferred, more preferred and most preferred parameters of the dispersive Raman embodiments of the invention.

TABLE A

HIGH CORRELATION DISPERSIVE RAMAN SPECTRAL REGIONS

| Physical Property | Units | Preferred | More Preferred | Most Preferred |
|---|---|---|---|---|
| Research Octane # | $cm^{-1}$ | 200–1900 | 1400–1900 | 500–800 900–1350 |
| Motor Octane # | $cm^{-1}$ | 200–1900 | 1400–1900 | 500–800 900–1350 |
| Pump Octane # | $cm^{-1}$ | 200–1900 | 1400–1900 | 500–800 900–1350 |
| Reid Vapor Pressure | $cm^{-1}$ | 200–1900 | 1500–1900 | 500–1500 |

Table B summarizes preferred, more preferred and most preferred parameters of the FT-Raman embodiments of the invention.

TABLE B

HIGH CORRELATION FT RAMAN SPECTRAL REGIONS

| Parameter | Units | Preferred | More Preferred | Most Preferred* |
|---|---|---|---|---|
| Research Octane # | $cm^{-1}$ | 200–1900, 2500–3300 | 200–1900 | 2500–3300 |
| Motor Octane # | $cm^{-1}$ | 200–1900, 2500–3300 | 200–1900 | 2500–3300 |
| Pump Octane # | $cm^{-1}$ | 200–1900, 2500–3300 | 200–1900 | 2500–3300 |
| Reid Vapor Pressure | $cm^{-1}$ | 200–1900, 2500–3300 | 200–1900 | 2500–3300 |

*In the case of highly fluorescent samples, this region is the most preferred

Table C summarizes preferred, more preferred and most preferred parameters of the spectral pre-processing of the invention.

TABLE C

PREFERRED SPECTRAL PREPROCESSING TECHNIQUES

| Method | Preferred | More Preferred | Most Preferred |
|---|---|---|---|
| Ft-Raman | mean-centered, variance scaled | mean-centered | variance scaled |
| Dispersive Raman | first-derivative | mean-centered, variance scaled | mean-centered |

DESCRIPTION OF THE PREFERRED EMBODIMENTS

EXAMPLE 1

A set of 208 gasoline blends from the Ashland Petroleum Company, Catlettsburg refinery are sealed in 6 dram glass vials with Teflon lined caps. Headspaces in the vials are kept to a minimum. The samples are shipped overnight and upon arrival at Old Dominion University, they are immediately placed in an explosion-proof freezer maintained at –18° C. Prior to shipment, the samples are stored by Ashland at –40° C. for several months. During this time, the motor and research octane numbers are experimentally determined using current ASTM knock engine methods (ASTM method D2699 for determination of RON and ASTM method D2700 for determination of MON). In addition, the Reid Vapor Pressure (RVP) is determined for 201 of the 208 samples. The Reid Vapor Pressure bomb is equilibrated at 38° C., and the vapor pressure is measured and corrected for barometric pressure via the Grabner Method.

Each octane number is determined at four different knock engine laboratories (Ashland knock engine labs in St. Paul, Minn.; Canton, Ohio; Ashland, Ky.; and Catlettsburg, Ky.). The average standard deviation for all of the samples is ~0.4 octane numbers.

The Raman spectra of the 208 samples are acquired using a Nicolet 950 FT-Raman spectrometer. A 180 degree collection geometry is used. Prior to spectral acquisition, a sample is removed from the freezer, warmed until no condensation appears on the container, and is placed in the sample holder. The Nd:Yag laser (1064 nm) is focused through the glass to the center of the container. The laser power incident on the glass container wall ranges from a high value of 380 mW to a low value of 356 mW. Although it is possible to maintain laser power at the sample at a constant value, the slight variations better approximate the fluctuations which might be expected in a "real world" application. Each spectrum consists of 200 scans, collected over 110 seconds at 8 $cm^{-1}$ resolution with Happ-Genzel apodization being used in the transformation. All spectra are mean-centered and variance-scaled and subsequently processed using Quant-IR partial least squares software (Nicolet).

Figure 1:
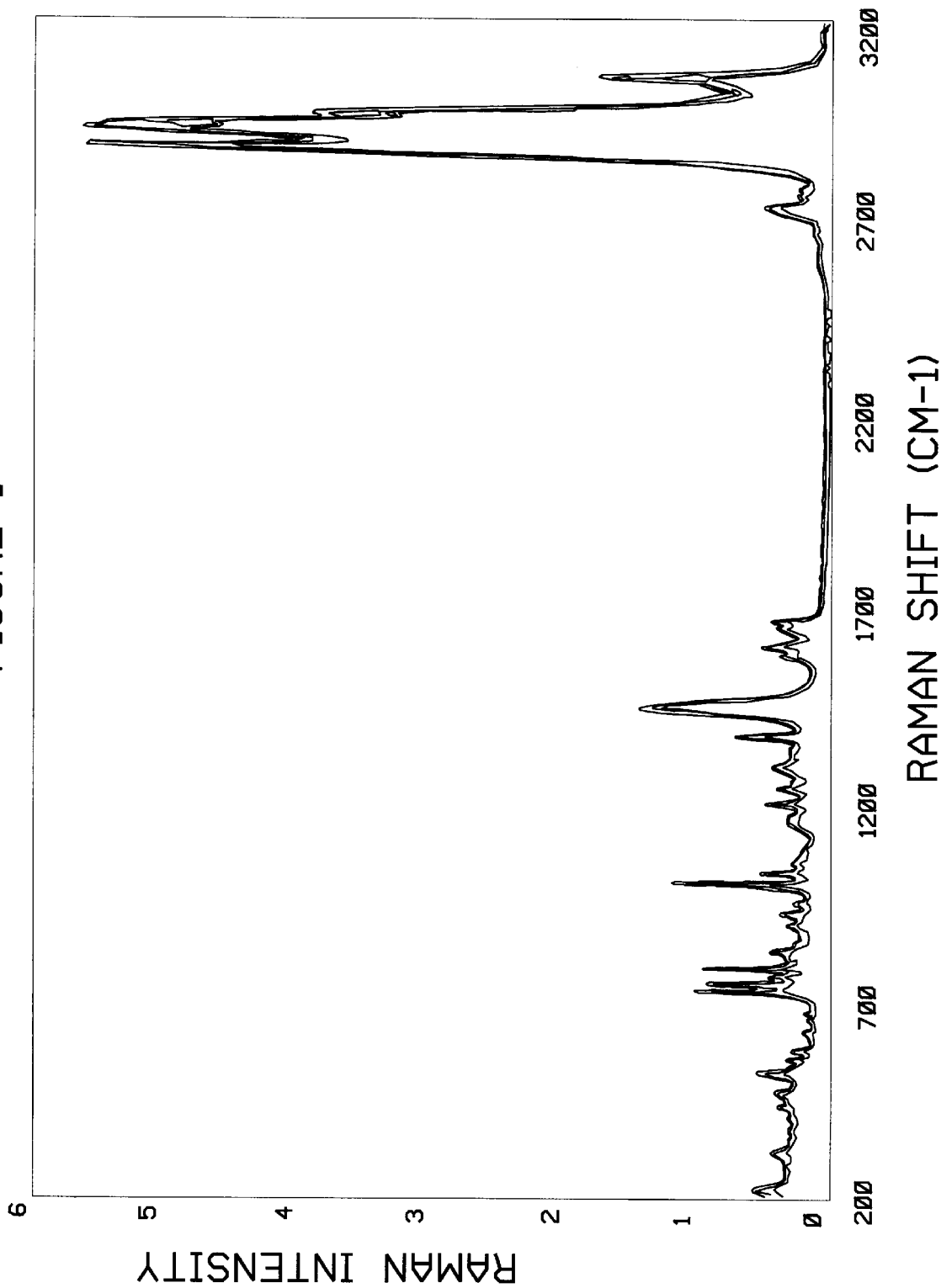
FIG. 1 is a plot of five overlaid FT-Raman spectra of commercial petroleum fuels. These spectra are representative of the majority of the 208 petroleum fuels.
Figure 2:
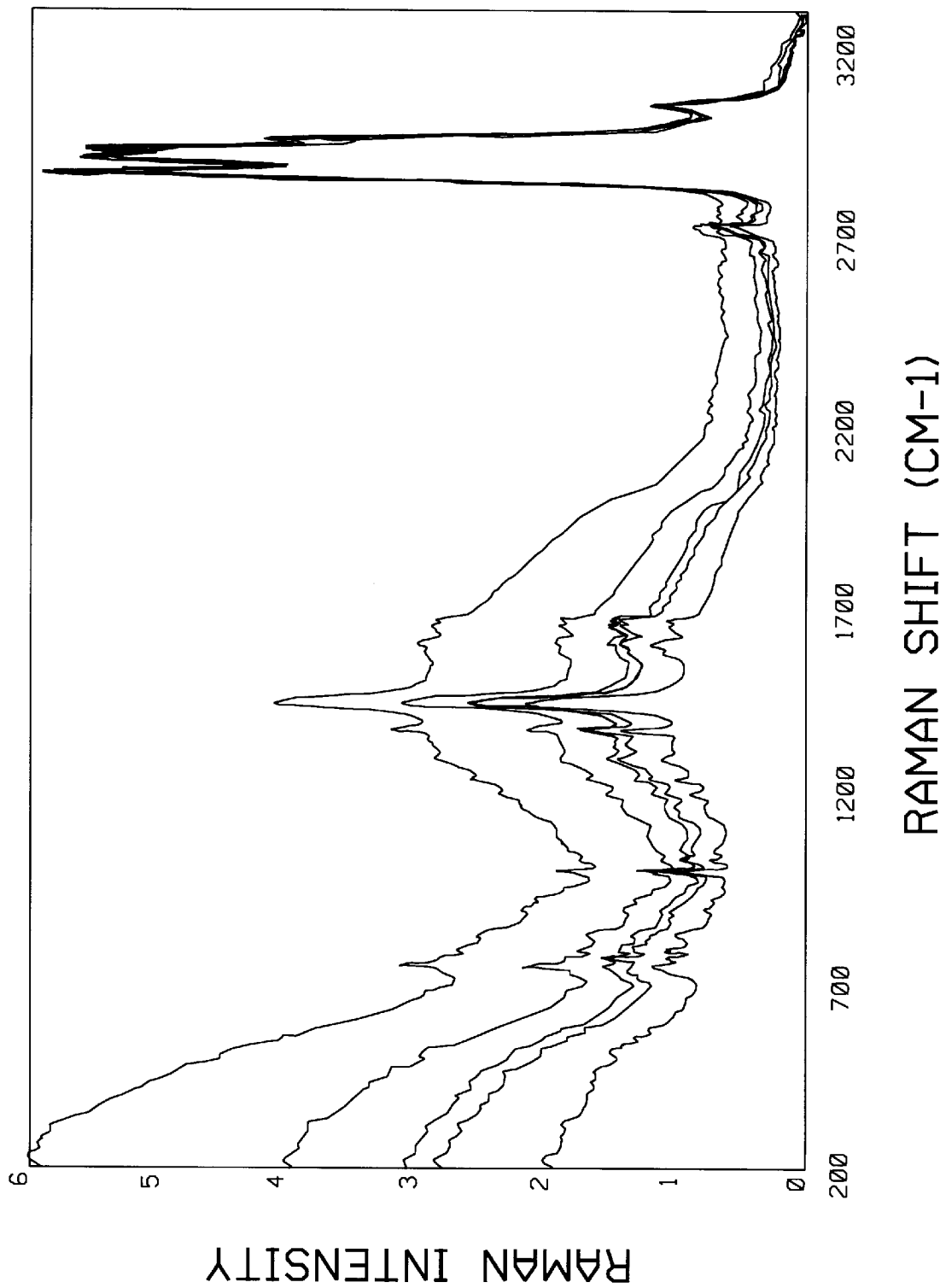
FIG. 2 is a plot of FT-Raman spectra of the five fluorescent commercial petroleum fuels. Of the 208 fuels, these are the only five which fluoresce when excited with 1064 nm radiation.
Figure 3:
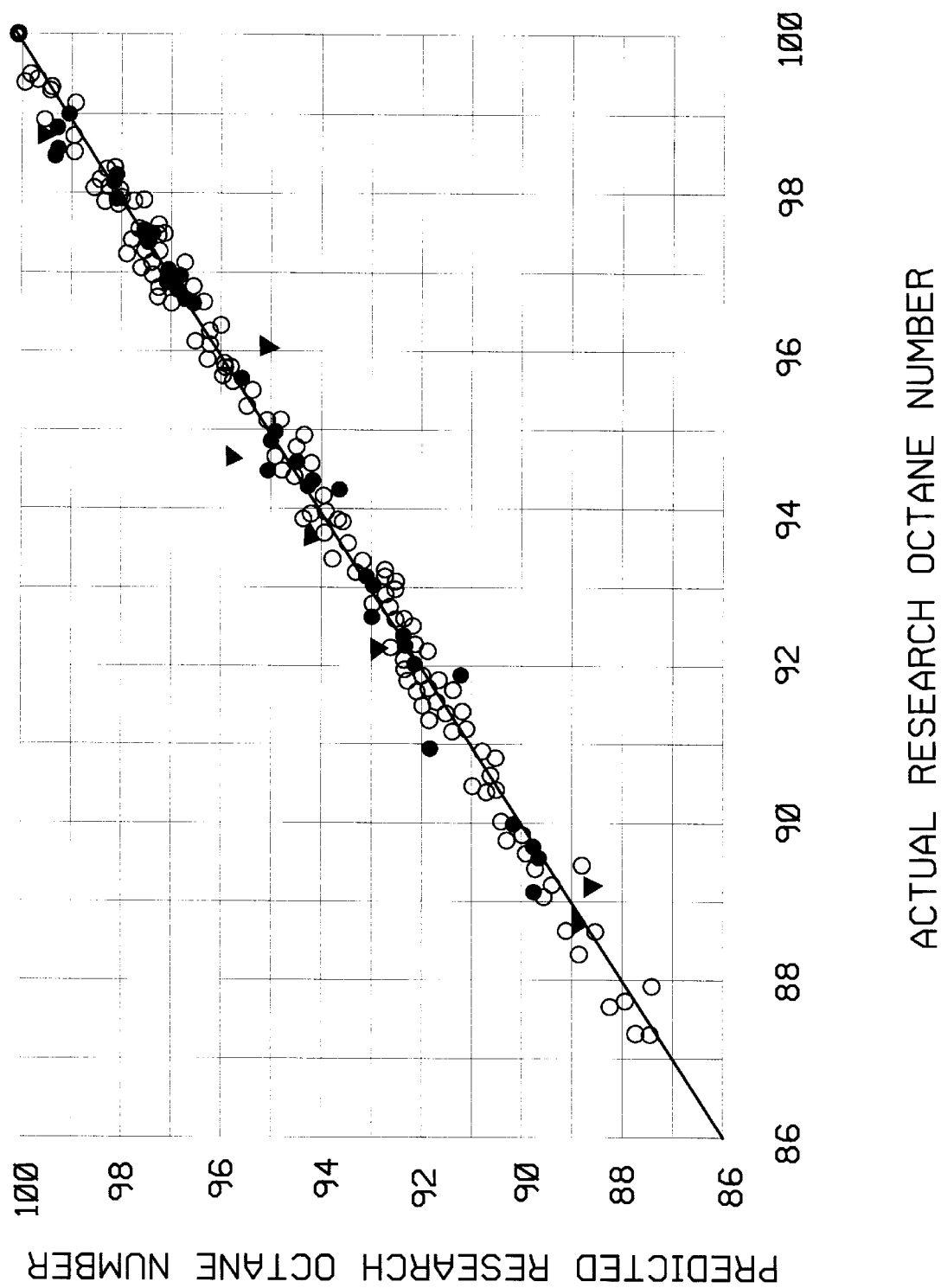
FIG. 3 is a plot of predicted vs. actual Research Octane Number, based on models developed from FT-Raman spectra as described in Example 1. Open circles (total of 175) correspond to samples which are included in the training set, the filled circles (total of 20) correspond to samples in the test set, and the filled triangles (total of 8) correspond to highly leveraged samples (outliers) which are removed from the training set prior to constructing the partial least squares regression model.
Figure 4:
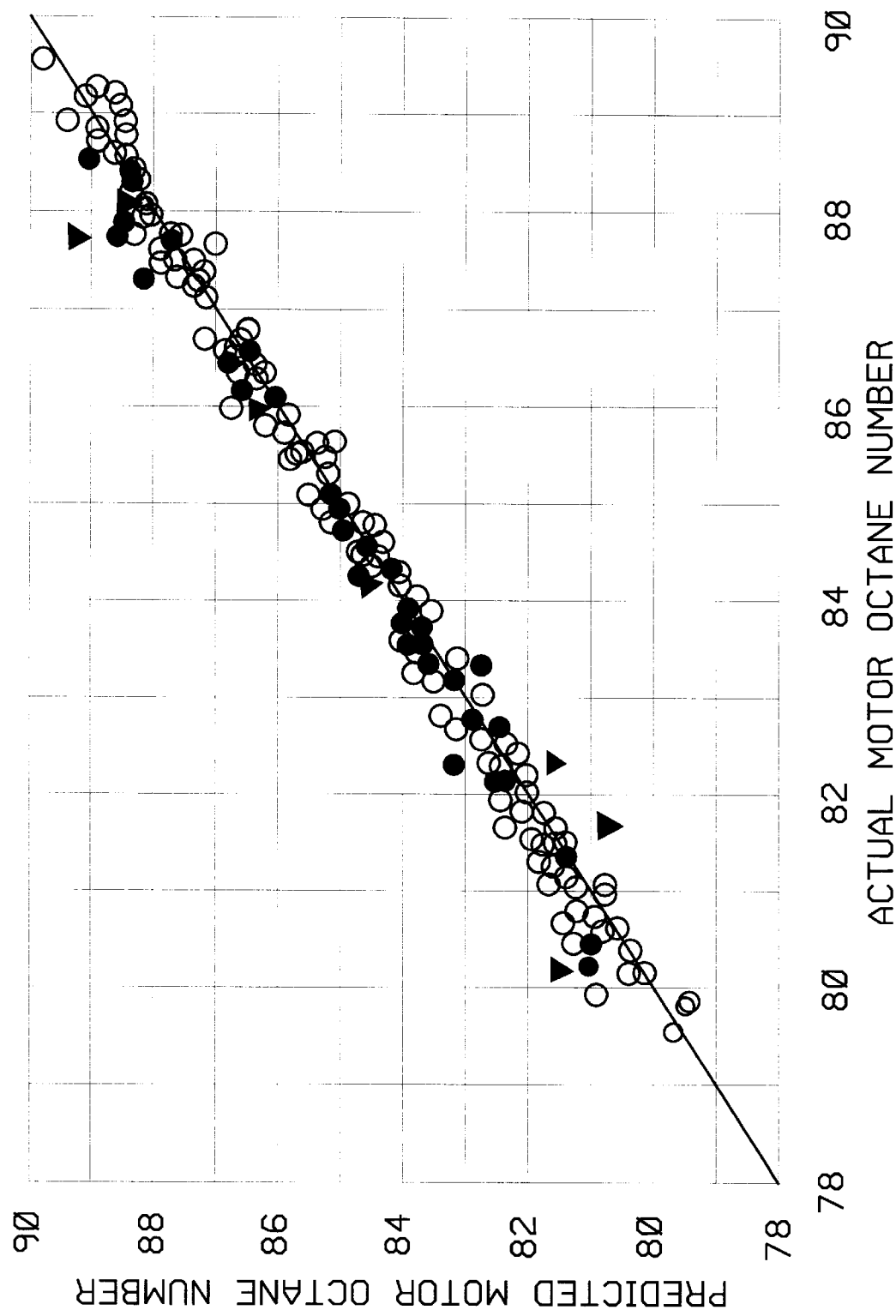
FIG. 4 is a plot of predicted vs. actual Motor Octane Number, based on models developed from FT-Raman spectra as described in Example 1. Open circles (total of 175) correspond to samples which are included in the training set, the filled circles (total of 20) correspond to samples in the test set, and the filled triangles (total of 8) correspond to highly leveraged samples which are removed from the training set prior to constructing the partial least squares regression model.
Figure 5:
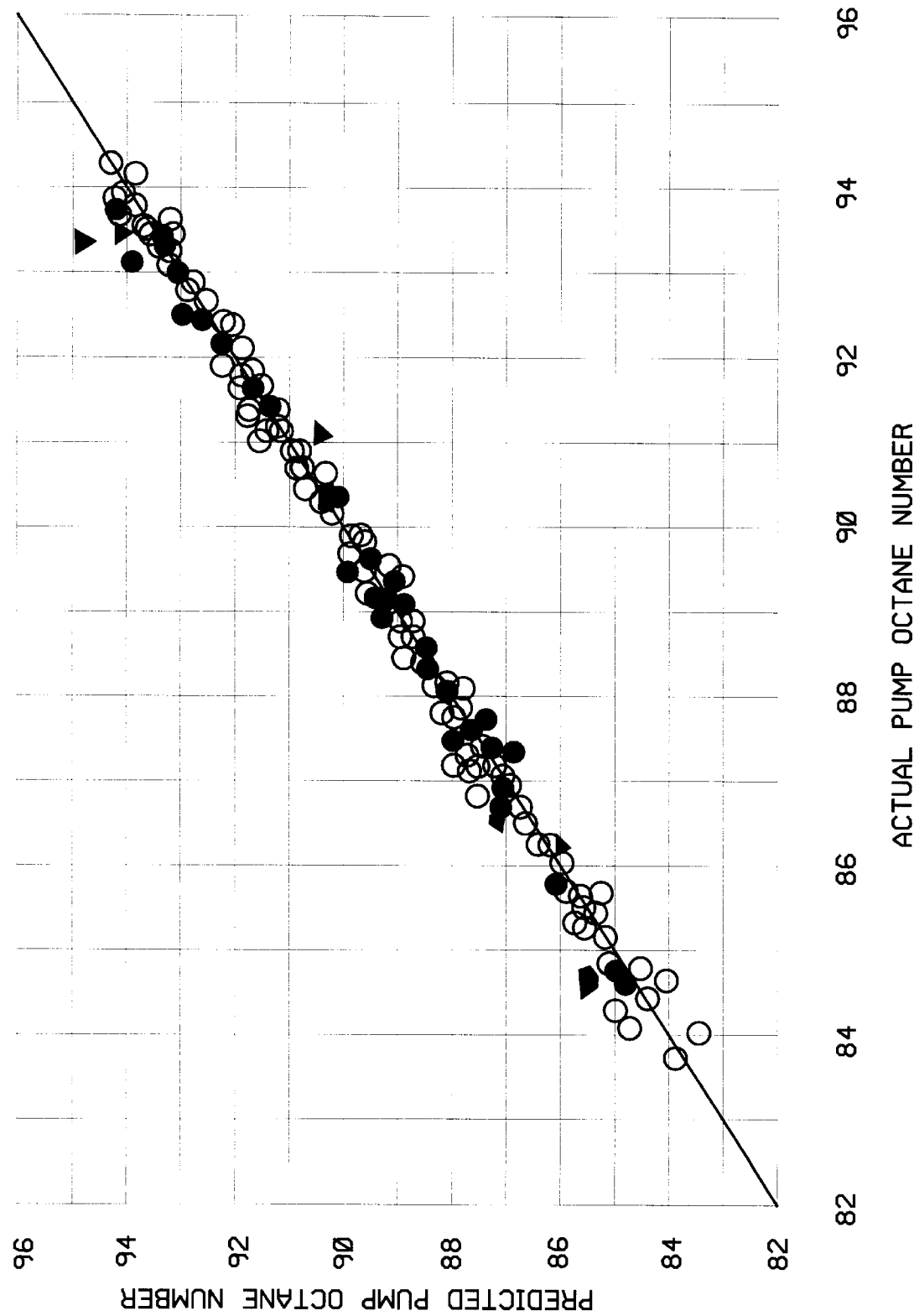
FIG. 5 is a plot of predicted vs. actual Pump Octane Number, based on models developed from FT-Raman spectra as described in Example 1. Open circles (total of 175) correspond to samples which are included in the training set, the filled circles (total of 20) correspond to samples in the test set, and the filled triangles (total of 8) correspond to highly leveraged samples which are removed from the training set prior to constructing the partial least squares regression model.

FIG. 1 shows the FT-Raman spectra for five of the 208 petroleum fuels. These samples are representative of the majority of samples received. For octane analysis, the petroleum fuels are divided into two groups. One group (the training set) consisted of 188 petroleum fuels, and the other group (the test set) consisted of 20 fuels. The subdivision into two groups is random and is performed prior to any partial least squares analysis. The Raman spectra for each of the samples in the training set are taken, and are used to construct partial least squares regression models correlating the Raman spectra with the octane numbers for each sample. In these models, two Raman spectral regions are used: 2570–3278 $cm^{-1}$ and 196–1851 $cm^{-1}$. From these regression models, it is evident that the model-predicted octane values for five samples consistently show large deviations from their experimentally determined values. The Raman spectra for these samples are shown in FIG. 2. These spectra differ dramatically from those of the remaining samples. The difference is due to a weak fluorescent background which decreases to zero in the CH stretching region of the spectra. These samples are removed from the training set and new regression models are constructed. Leverage plots for the resulting models are used to eliminate eight additional spectra from the training set, bringing the total number of standards to 175 for RON, MON, and PUMP models. The predicted vs. actual octane plots for RON, MON, and PUMP are given in FIGS. 3, 4, and 5, respectively. These plots include the predicted values for the eight most leveraged samples which are removed from the training set (plotted as filled triangles). Table 1 includes the number of factors included in each of the models as well as the standard error of validation (SEV) using the leave-one-out validation method.

TABLE 1

| Determined | Low | High | No of | SEV[1] | SEV[2] |
| --- | --- | --- | --- | --- | --- |
| MON | 79.56 | 89.55 | 175 | 0.415 | 0.77 |
| RON | 87.33 | 99.95 | 175 | 0.535 | 0.42 |
| Pump | 83.74 | 94.288 | 175 | 0.41 | 0.52 |
| RVP (psi) | 7.07 | 14.735 | 175 | 0.568 | 0.60 |

[1]Standard Error Validation for FT Raman Spectroscopy

In addition to using leave-one-out validation for the regression models, the models are also used to predict the octane numbers of the test set. These results are plotted in FIGS. 3, 4, and 5 (the test set values are plotted as solid circles).

Figure 6:
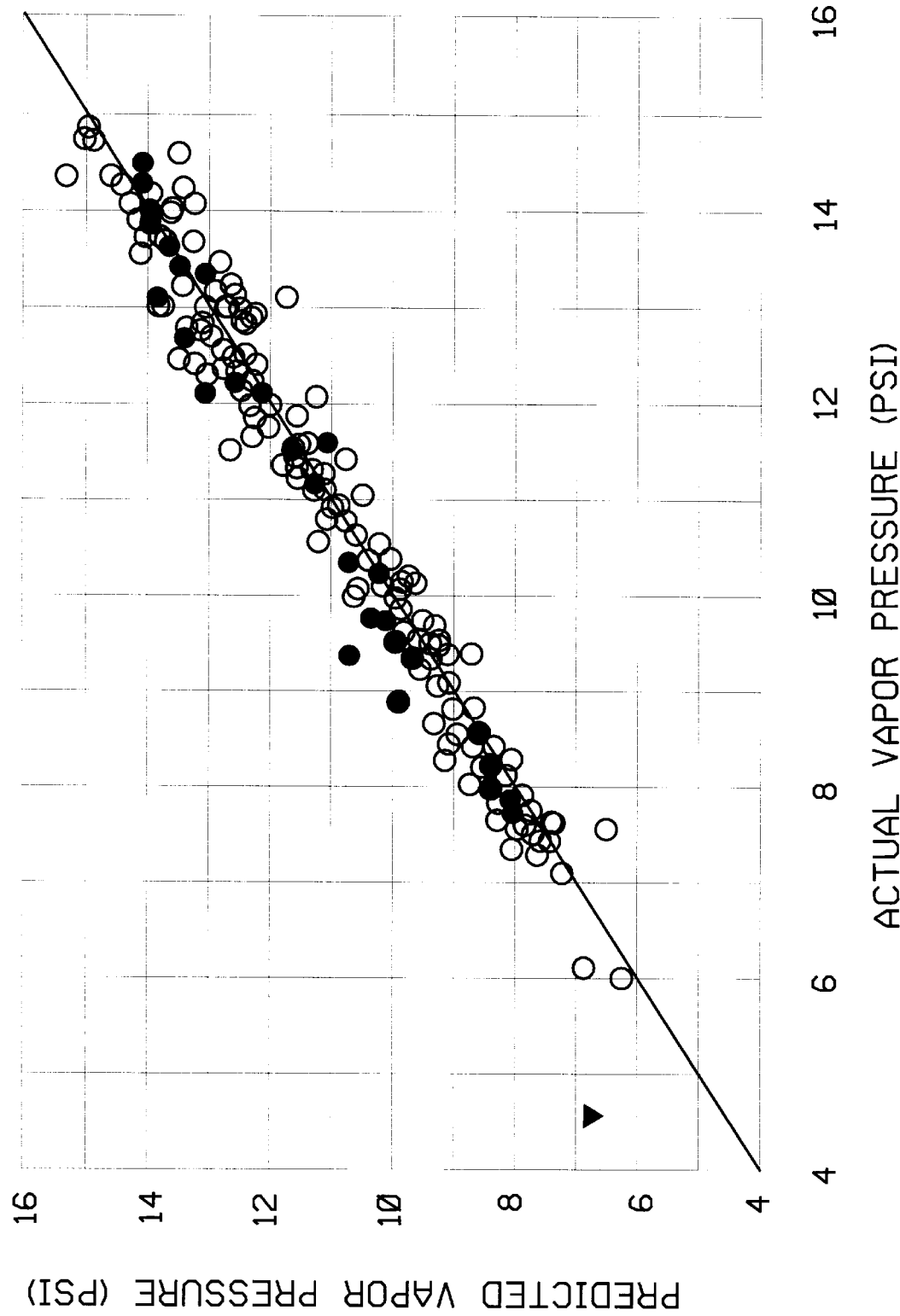
FIG. 6 is a plot of predicted vs. actual Plot for Reid Vapor Pressure, based on models developed from FT-Raman spectra as described in Example 1. Open circles (total of 175) correspond to samples which are included in the training set, the filled circles (total of 20) correspond to samples in the test set, and the filled triangle corresponds to a highly leveraged sample which are removed from the training set prior to constructing the partial least squares regression model.
Figure 7A:
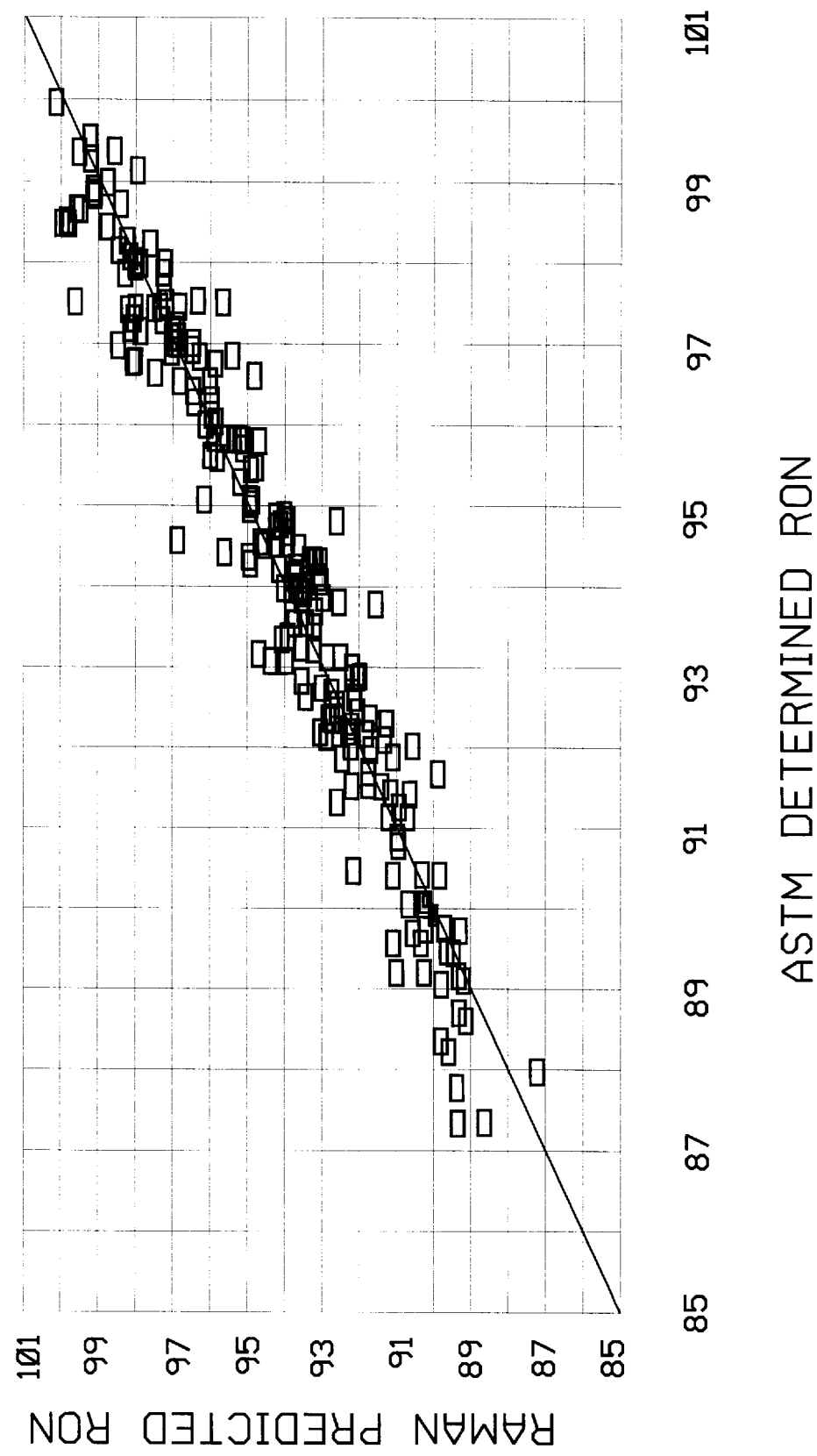
FIG. 7a is a plot of Predicted vs. Actual Research Octane Number (RON), based on models developed from dispersive Raman spectra obtained as described in Example 3.
Figure 7B:
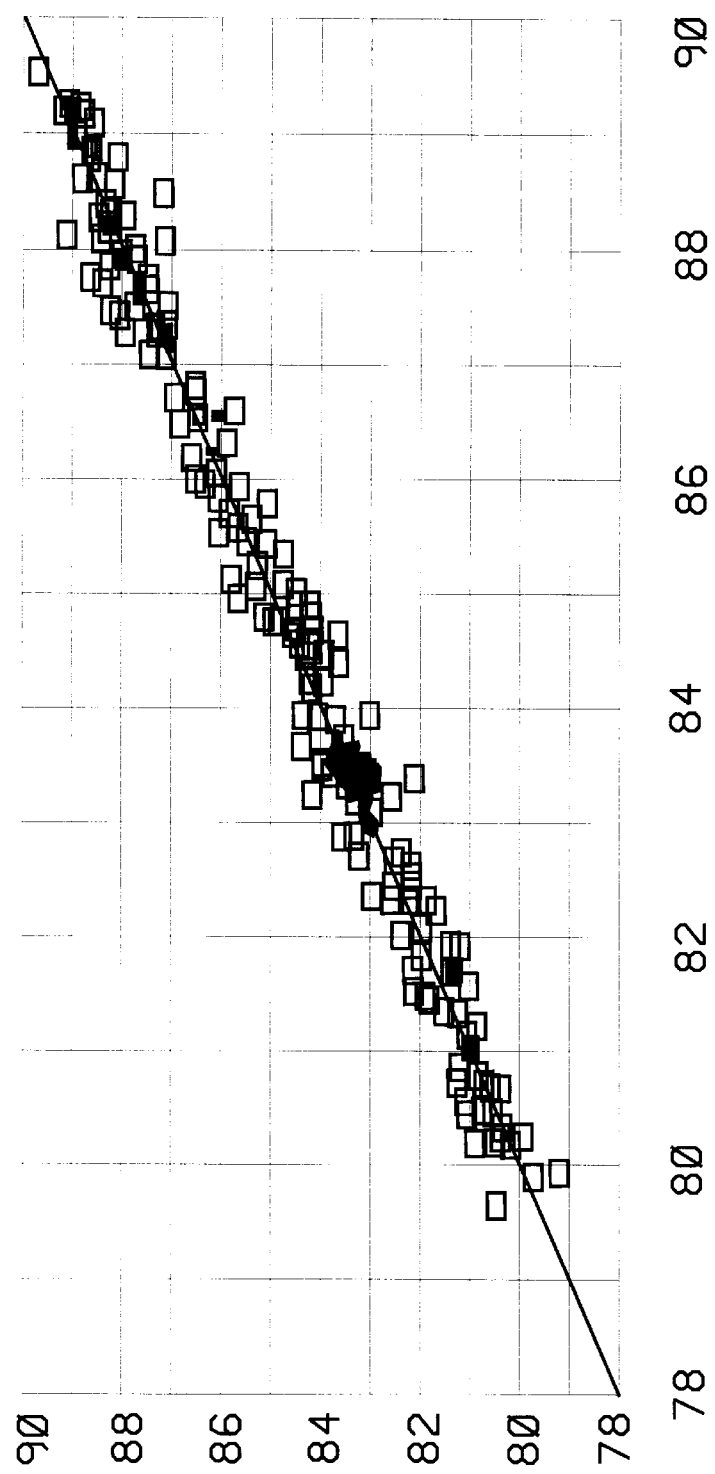
FIG. 7b is a plot of Predicted vs. Actual Motor Octane Number (MON), based on models developed from dispersive Raman spectra obtained as described in Example 3.
Figure 7C:
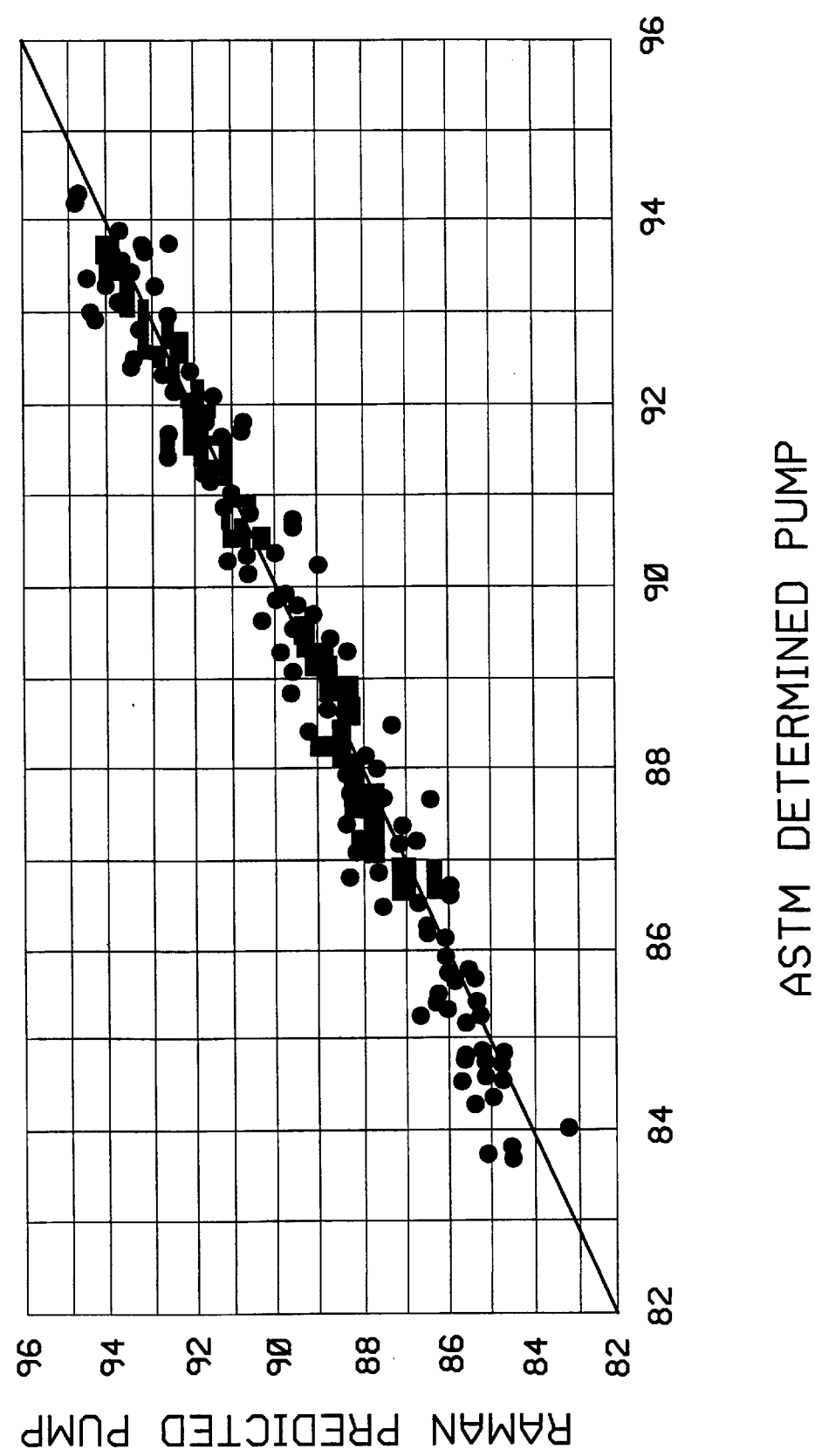
FIG. 7c is a plot of Predicted vs. Actual Pump Octane Number, based on models developed from dispersive Raman spectra obtained as described in Example 3.
Figure 7D:
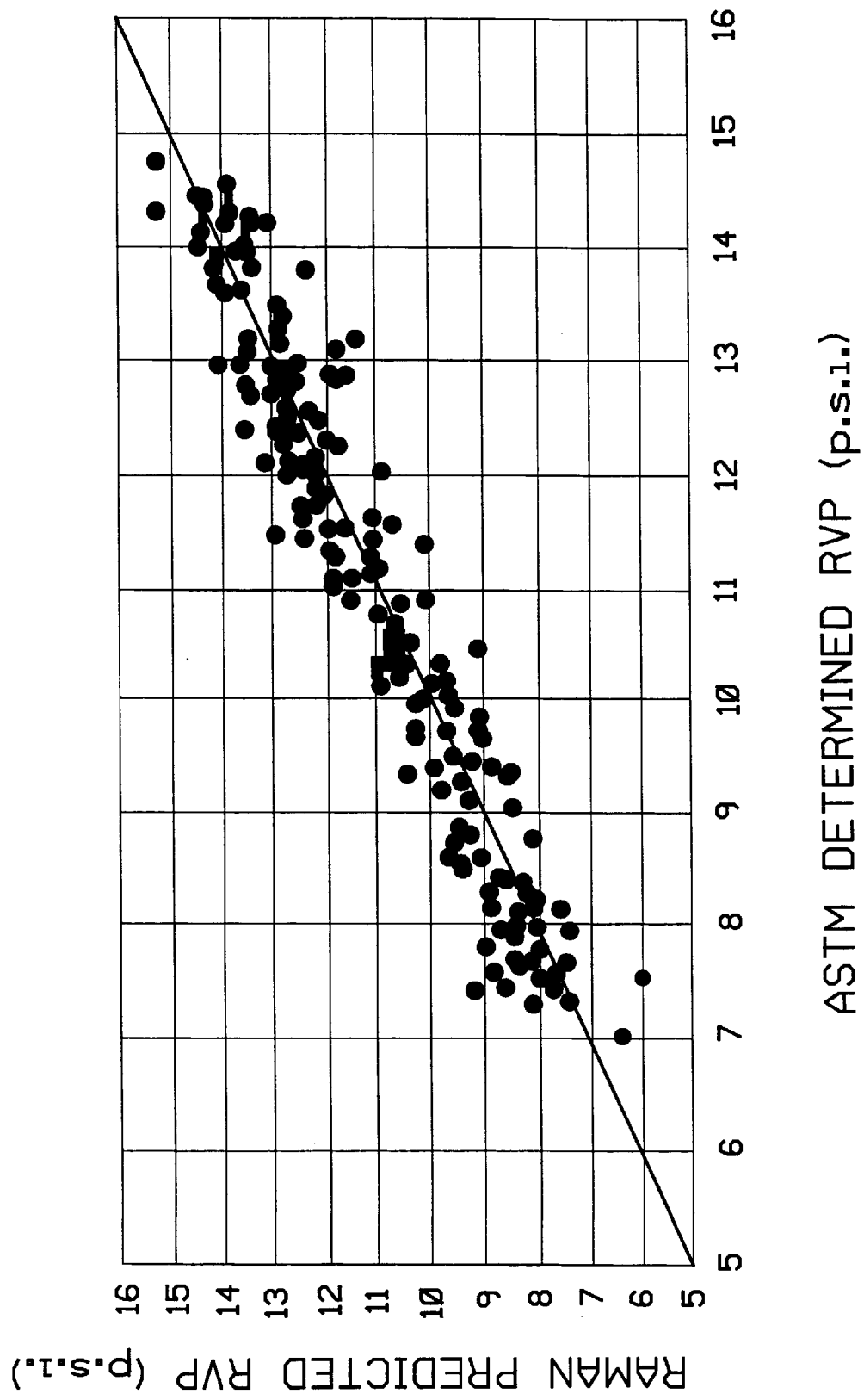
FIG. 7d is a plot of Predicted vs. Actual Reid Vapor Pressure, based on models developed from dispersive Raman spectra obtained as described in Example 3.

The above described procedures are also used to construct models which correlate the Reid Vapor Pressure with the Raman spectra. Of the 208 samples, only 201 have experimentally determined Reid Vapor Pressures associated with them. The training set consists of 175 samples (the five fluorescent samples and one highly leveraged sample being removed from the 201 samples) and the remaining 20 samples are used as the test set and are identical to the test set used for the octane determinations. The predicted vs. actual values for the resulting model constructed from the 175 standards are plotted in FIG. 6, where the test set values correspond to solid circles.

EXAMPLE 2

Referring to FIG. 2, using techniques similar to those of Example 1, the spectra of FIG. 2 are obtained using 5 fluorescent commercial petroleum fuels. Of the 208 fuels tested, these are the only 5 which fluoresce when excited with 1064 nm radiation.

For the fluorescent samples, the background under the CH stretching region is linear. Hence, a separate regression model is constructed using only the 2510–3278 $cm^{-1}$ region. This regression model did not contain the fluorescent samples in the training set. Once this model is constructed, the model is used to predict the octane numbers for the fluorescent samples. These values are given in Table 2 along with values for models constructed using the entire spectral region (196–3278 $cm^{-1}$) and the spectral regions used in the octane models (2510–3278 and 196–1851 $cm^{-1}$).

TABLE 2

Predicted Values for Five Fluorescent Petroleum Samples Using Various Spectral Regions

| Sample Number | RON actual | Entire Spectrum[a] | 2 Spectral Regions[b] | C–H Region[c] |
|---|---|---|---|---|
| 175 | 94.66 | 141.43 | 103.51 | 95.29 |
| 176 | 88.61 | 110.50 | 93.19 | 89.06 |
| 177 | 94.80 | 127.14 | 101.10 | 95.20 |
| 179 | 93.97 | 107.34 | 96.76 | 94.78 |
| 209 | 94.57 | 115.74 | 95.94 | 92.94 |

MON Model Predicted Values

| Sample Number | MON actual | Entire Spectrum[a] | 2 Spectral Regions[b] | C–H Region[c] |
|---|---|---|---|---|
| 175 | 85.02 | 116.89 | 87.15 | 85.31 |
| 176 | 80.45 | 93.71 | 80.67 | 80.10 |
| 177 | 85.16 | 105.44 | 86.63 | 85.78 |
| 179 | 83.63 | 93.07 | 84.39 | 83.98 |
| 209 | 83.13 | 97.70 | 83.16 | 82.76 |

PUMP Model Predicted Values

| Sample Number | Pump actual | Entire Spectrum[a] | 2 Spectral Regions[b] | C–H Region[c] |
|---|---|---|---|---|
| 175 | 89.82 | 117.99 | 103.74 | 89.88 |
| 176 | 84.53 | 96.87 | 90.32 | 84.71 |
| 177 | 89.98 | 109.09 | 99.06 | 90.63 |
| 179 | 88.80 | 97.24 | 92.71 | 89.38 |
| 209 | 88.85 | 101.03 | 93.57 | 87.88 |

RVP Model Predicted Values

| Sample Number | RVP(psi) actual | Entire Spectrum[a] | 2 Spectral Regions[b] | C–H Region[c] |
|---|---|---|---|---|
| 175 | 10.80 | 31.97 | 42.64 | 9.44 |
| 176 | 10.40 | 18.78 | 23.79 | 9.40 |
| 177 | 11.32 | 23.69 | 30.12 | 10.44 |
| 179 | 11.68 | 18.93 | 21.87 | 11.82 |
| 209 | 13.07 | 21.37 | 27.03 | 12.29 |

[a] 196–3278 $cm^{-1}$
[b] 196–1851 and 2510–3278 $cm^{-1}$
[c] 2510–3278 $cm^{-1}$

EXAMPLE 3

Radiation (852 nm) from a distributed Bragg reflector (DBR) GaAlAs diode laser (Spectra Diode Labs) is filtered with a dielectric band pass filter (Janos Technology) and launched into a 200/220 micron quartz fiber-optic (Polymicro Inc.). The DBR laser has recently been shown to be superior to regular, Fabry-Perot index guided lasers. Due to an internal grating, DBR lasers do not give rise to mode hops or frequency hysteresis, and may therefore be ideal for long term industrial process control operations.

The fiber-optic system consists of an excitation fiber, two meters long, which delivers laser radiation to the sample. Close packed around the excitation fiber are six collection fibers which gather the Raman scattered light. About four inches of the end of this fiber-optic bundle, the probe, was sealed into an aluminum tube and polished. Light from the proximal ends of the collection fibers was collimated with an $f/2$ plano-convex NIR reflection coated lens and filtered with an 852 nm holographic notch filter (Kaiser Optical) to remove Rayleigh scatter. The Raman signal was focused onto the slits (70 micron slit width) of a ¼ meter spectrograph $f/4$ (Chromex) with an $f/4$ lens. A 300 groove/mm grating, blazed at 1 micron, dispersed the Raman signal.

An ST6 - UV CCD (Santa Barbara Instruments Group) thermoelectrically cooled to $-35°$ C. detected the dispersed signal. The detector consists of 350 vertical pixels and 750 horizontal pixels. The pixels were binned by 350 in the vertical direction and by 2 in the horizontal. The Raman spectra were acquired by placing the probe against the sample vial and integrating for 60 seconds. All samples were analyzed during a 10-hour period. The laser was operated at a current of 150 mA, giving an incident power at the sample of ~50 mW. Spectral processing and PLS regression analysis was accomplished with Pirouette multivariate software.

Research octane numbers (ASTM Method 2699-94), motor octane numbers (ASTM Method 2700-94), pump octane number, PUMP=(MON+RON )/2, and the REID vapor pressures (Grabner Method) were determined for each of the samples nine months prior to the Raman analysis. For the gasoline samples, the octane numbers ranged from 79.5–99.5 octane numbers and the Reid vapor pressures ranged from 7–15 psi The samples were sealed in glass vials with Teflon lined caps and stored in an explosion proof freezer at $-18°$ C. until analysis.

Partial least squares analysis is used to regress the spectra against the knock-engine determined octane numbers. The regressions were performed and validated by the leave-one-out method. Preprocessing techniques included mean centering, mean centering combined with variance scaling (autoscaling), and a first derivative transformation combined with mean centering.

The standard errors of validation (SEV) for the resulting models are given in Table 1. for comparison with the FT-Raman results of Example 1. All four physical properties of the gasolines are highly correlated with the Raman spectra. Plots showing the Predicted vs. Measured octane rating are shown in FIGS. 7a–7d.

MODIFICATIONS

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein.

Examples include an apparatus for controlling a process comprising in combination: a) sample source means comprising a mixture of a plurality of hydrocarbons and operably communicating with; b) fiber-optic dispersive Raman spectroscopy means having a CCD detection means and infrared diode laser excitation means, connected to; c) signal emitting means for emitting a signal indicative of absorbance in at least one wavelength, communicating with; d) mathematical manipulation means for processing the signal to model physical and/or chemical properties of the sample and to provide a processed signal; and e) process control means responsive to the processed signal. Preferred is an apparatus in which the mathematical manipulation means employs partial least squares regression analysis, the sample source comprises a feed flowing into a physical or chemical process or product produced by the process. Also in the examples is an apparatus in which the process comprises a blending of two or more hydrocarbons, the process comprises a reforming, cracking, lube oil production, hydrotreating, or other petroleum refining process, and Raman spectroscopy means comprises a Distributed Bragg Laser means, and the mathematical manipulation comprises the use of loading vectors. An illustration of an apparatus including fiber optic dispersive Raman spectroscopy means having laser excitation means, signal emitting means, and CCD detector means is shown in FIG. 2 of the aforementioned U.S. Ser. No. 449,326, now U.S. Pat. No. 5,596,196.

Reference to documents made in the specification is intended to result in such patents or literature being expressly incorporated herein by reference.

What is claimed is:

1. A process for determination of motor, research, or pump octane number of a liquid fuel mixture comprising
    a) irradiating a sample of a liquid fuel mixture comprising hydrocarbons to produce scattered Raman radiation emitted from the sample;
    b) collecting Raman scattered radiation emitted from the sample;
    c) dispersing or transforming the collected Raman scattered radiation from the sample into sample spectra with intensities corresponding to the motor, research, or pump octane number of said liquid fuel mixture;
    d) processing said sample spectra according to a regression model derived by multivariate analysis of Raman spectra, or mathematical function thereof, of liquid mixtures of known motor, research, or pump octane numbers to determine the motor, research, or pump octane of the liquid fuel mixture.

2. The process of claim 1 wherein the liquid fuel mixture is a hydrocarbon mixture and the sample is irradiated with near infrared radiation.

3. The process of claim 2 wherein steps a, b and c are performed in apparatus selected from a Fourier-Transform Raman spectrometer, a dispersive Raman spectrometer, and a Hadamard Transform Raman spectrometer.

4. The process of claim 2 in which the processing of said sample spectra utilizes only CH stretching spectral region, which is baseline corrected, of said sample spectra.

5. A process for determination of Reid Vapor Pressure of a liquid fuel mixture comprising
    a) irradiating a sample of a liquid fuel mixture comprising hydrocarbons to produce scattered Raman radiation emitted from the sample;
    b) collecting Raman scattered radiation emitted from the sample;
    c) dispersing or transforming the collected Raman scattered radiation from the sample into sample spectra with intensities corresponding to Reid Vapor Pressure of said liquid fuel mixture;
    d) processing said sample spectra according to a regression model derived by multivariate analysis of Raman spectra, or mathematical function thereof, of liquid mixtures of known Reid Vapor Pressures to determine the Reid Vapor Pressure of the liquid fuel mixture.

6. The process of claim 5 wherein the liquid mixture is a hydrocarbon mixture and the sample is irradiated with near-infrared radiation.

7. The process of claim 6 wherein steps a, b and c are performed in apparatus selected from a Fourier-Transform Raman spectrometer, a dispersive Raman spectrometer, and a Hadamard Transform Raman spectrometer.

8. The process of claim 6 in which the processing of said sample spectra utilizes only CH stretching spectral region, which is baseline corrected, of said sample spectra.

9. A process comprising
    a) irradiating a sample of a liquid fuel mixture comprising hydrocarbons to produce scattered Raman radiation emitted from the sample;
    b) collecting Raman scattered radiation emitted from the sample;
    c) dispersing or transforming the collected Raman scattered radiation from the sample into sample spectra with intensities corresponding to the motor, research, or pump octane number of said liquid fuel mixture;
    d) processing said sample spectra according to a regression model derived by multivariate analysis of Raman spectra, or mathematical function thereof, of liquid mixtures having known motor, research, or pump octane numbers, and producing a control signal representative of the motor, research, or pump octane number of the liquid fuel mixture;
    e) controlling a process in response to said control signal.

10. The process of claim 9 wherein the liquid fuel mixture is a hydrocarbon mixture and the sample is irradiated with near-infrared radiation.

11. The process of claim 10 in which the processing of said sample spectra utilizes only CH stretching spectral region, which is baseline corrected, of said sample spectra.

12. The process of claim 9 wherein the hydrocarbon mixture comprises oxygenated hydrocarbons.

13. A process comprising
    a) preparing multiple samples of liquid fuel mixtures each comprising one or more hydrocarbons as components in varying concentrations;
    b) irradiating the respective samples of said liquid fuel mixtures individually with near-infrared radiation, producing scattered Raman radiation emitted from each sample;
    c) collecting Raman scattered radiation emitted from each of the samples;

d) dispersing or transforming the collected Raman scattered radiation from each of the samples into spectra with intensities corresponding to the motor, research, or pump octane numbers of the mixture;

e) performing multivariate analysis on said spectra, or mathematical functions thereof, to derive a regression model representative of the mixtures.

14. The process of claim 13 wherein the liquid fuel mixtures comprise hydrocarbon mixtures.

15. A process comprising
 a) preparing multiple samples of liquid fuel mixtures each comprising one or more hydrocarbons as components in varying concentrations;
 b) irradiating the respective samples of said liquid fuel mixtures individually with near-infrared radiation, producing scattered Raman radiation emitted from each sample;
 c) collecting Raman scattered radiation emitted from each of the samples;
 d) dispersing or transforming the collected Raman scattered radiation from each of the samples into spectra with intensities corresponding to the Reid Vapor Pressure of the mixture;
 e) performing multivariate analysis on said spectra, or mathematical functions thereof, to derive a regression model representative of the mixtures.

16. The process of claim 15 wherein the liquid fuel mixtures comprise hydrocarbon mixtures.

17. A process comprising
 a) recovering multiple samples of liquid mixtures, each comprising one or more hydrocarbons as components in varying concentrations;
 b) analyzing at least a portion of the samples to determine the components therein and their concentrations;
 c) irradiating the respective samples of said mixtures individually with near-infrared radiation, producing scattered Raman radiation emitted from each sample;
 d) collecting Raman scattered radiation emitted from each of the samples;
 e) dispersing or transforming the collected Raman scattered radiation from each of the samples into sample spectra with intensities corresponding to the motor, research, or pump octane of each of said samples;
 f) performing multivariate analysis on said spectra or mathematical functions thereof to derive a regression model for determining motor, research, or pump octane numbers of mixtures containing one or more hydrocarbons in varying concentrations.

18. The process of claim 17 wherein the liquid mixtures comprise hydrocarbon mixtures.

19. The process of claim 18 in which the processing of said sample spectra utilizes only CH stretching spectral region, which is baseline corrected, of said sample spectra.

20. A process comprising
 a) recovering multiple samples of liquid mixtures, each comprising one or more hydrocarbons as components in varying concentrations;
 b) analyzing at least a portion of the samples to determine the components therein and their concentrations;
 c) irradiating the respective samples of said mixtures individually with near-infrared radiation, producing scattered Raman radiation emitted from each sample;
 d) collecting Raman scattered radiation emitted from each of the samples;
 e) dispersing or transforming the collected Raman scattered radiation from each of the samples into spectra with intensities corresponding to Reid Vapor Pressure of each of said samples;
 f) performing multivariate analysis on said spectra or mathematical functions thereof to derive a regression model for determining Reid Vapor Pressure of mixtures containing one or more hydrocarbons in varying concentrations.

21. The process of claim 20 wherein the liquid fuel mixtures comprise hydrocarbon mixtures.

22. A method of controlling a process for the production of a liquid fuel of desired research, motor, or pump octane comprising, periodically or continuously,
 a) irradiating a liquid sample of the process with near-infrared radiation from a near infrared source, said liquid fuel containing one or more hydrocarbons as components in varying concentrations, producing scattered Raman radiation emitted from the sample;
 b) collecting Raman scattered radiation emitted from the sample;
 c) transferring collected Raman scattered radiation and dispersing or transforming the collected Raman scattered radiation from the sample into sample spectra with intensities corresponding to the motor, research, or pump octane of said sample;
 d) determining the research, motor, or pump octane of the sample by processing the spectral intensities of said sample spectra according to a regression model derived by multivariate analysis of Raman spectra, or mathematical function thereof, of liquid mixtures of known motor, research, or pump octane numbers, the near infrared source radiation wavelength from said near-infrared source used in irradiating the sample being the same as or being correlated to that of the near-infrared source employed in establishing said model;
 e) controlling the process to produce said liquid fuel in response to the determined octane.

23. The process of claim 22 wherein the liquid sample comprises a hydrocarbon mixture.

24. The process of claim 23 in which the processing of said sample spectra utilizes only CH stretching spectral region, which is baseline corrected, of said sample spectra.

25. The process of claim 23 in which the near-infrared source employed in establishing said model is a laser source which produces a laser having intensity variation due to power variation, the intensity variation being compensated for in formation of said model by dividing at least one peak intensity acquired at a first laser power by the intensity of the same peak acquired under an extreme laser power to produce a ratio, and thereafter multiplying intensities in the spectrum acquired at the extreme laser power by the ratio.

26. A process for fuel blending to a desired research, motor, or pump octane comprising
 a) irradiating a liquid sample of a liquid fuel from a fuel blending process with near-infrared radiation from a near infrared source, said liquid fuel containing one or more hydrocarbons as components in varying concentrations, producing scattered Raman radiation emitted from said sample;
 b) collecting Raman scattered radiation emitted from the sample;
 c) transferring collected Raman scattered radiation and dispersing or transforming the collected Raman scattered radiation from the sample into sample spectra with intensities corresponding to the motor, research, or pump octane of said sample;

d) processing said sample spectra according to a regression model derived by multivariate analysis of Raman spectra, or mathematical function thereof, of liquid mixtures of known research, motor, or pump octane numbers, and outputting a periodic, intermittent or continuous signal indicative of the research, motor, or pump octane number of said sample;

e) inputting said signal to a means responsive thereto for controlling a fuel blending process.

27. The process of claim 26 wherein the signal is input to a means for controlling a reforming process.

28. The process of claim 26 wherein the signal is input to a means for controlling an aromatic extraction process.

29. The process of claim 26 wherein the signal is input to a means for controlling a distillation process.

30. The process of claim 26 wherein the signal is input to a means for controlling a fractionation process.

31. The process of claim 26 wherein the signal is input to a means for controlling a process for producing toluene.

32. The process of claim 26 wherein the signal is input to a means for controlling an aromatic disproportionation process.

33. The process of claim 26 wherein the dispersed or transformed spectra processed is a spectral region selected from 146–1851 $cm^{-1}$, 2570–3273, $cm^{-1}$ or a combination of these spectral regions.

34. The process of claim 26 wherein the dispersed or transformed spectra processed is a spectral region selected from 2500–3300 $cm^{-1}$.

35. The process of claim 26 wherein the dispersed or transformed spectra processed is a spectral region selected from 200–1900 $cm^{-1}$.

36. The process of claim 26 wherein the dispersed or transformed spectra processed is a spectral region selected From 200–1900 $cm^{-1}$, 2500–3300 $cm^{-1}$ or combination of these spectral regions.

37. The process of claim 26 in which the liquid sample comprises a hydrocarbon mixture, the near infrared source radiation wavelength from said near-infrared source used in irradiating the sample is the same as or is correlated to that of the near-infrared source employed in establishing said model, and the near-infrared source employed in establishing said model is a laser source which produces a laser having intensity variation due to power variation, the intensity variation being compensated for in formation of said model by dividing at least one peak intensity acquired at a first laser power by the intensity of the same peak acquired under an extreme laser power to produce a ratio, and thereafter multiplying intensities in the spectrum acquired at the extreme laser power by the ratio.

38. Apparatus for controlling a process for fuel blending comprising a) a sample source comprising a liquid fuel mixture of a plurality of hydrocarbons, said source operably communicating with b) fiber-optic dispersive Raman spectroscopy means having a CCD detection means and laser excitation means, said spectroscopy means connected to c) signal emitting means for emitting a signal indicative of Raman scattering corresponding to the motor, research, or pump octane numbers of the sample source, said signal emitting means communicating with d) mathematical manipulation means for processing the signal according to a regression model derived by multivariate analysis of Raman spectra, or mathematical function thereof, of liquid mixtures of known motor, research, or pump octane numbers, to determine the motor, research, or pump octane of the liquid fuel mixture and provide a processed signal and e) process control means communicating with the mathematical manipulation means responsive to the processed signal.

39. The apparatus of claim 38 in which the mathematical manipulation means employs partial least squares regression analysis.

40. The apparatus of claim 38 in which the sample source comprises a feed flowing into a physical or chemical process.

41. The apparatus of claim 38 in which the sample source comprises a product produced by the process.

42. The apparatus of claim 38 in which the process comprises a blending of two or more hydrocarbons.

43. The apparatus of claim 38 in which the process comprise a petroleum refining process.

44. The apparatus of claim 38 in which the process comprises a reforming, cracking, lube oil production, or hydrotreating process.

45. The apparatus of claim 38 in which the mathematical manipulation means comprises means for the use of loading vectors.

46. The apparatus of claim 38 in which variation in laser power of the laser excitation means is compensated for by dividing at least one peak intensity acquired at a first laser power by the intensity of the same peak acquired under a higher laser power to produce a ratio and thereafter multiplying intensities in the spectrum acquired at the higher laser power by the ratio.

* * * * *